(12) United States Patent
Hurd

(10) Patent No.: US 8,812,076 B2
(45) Date of Patent: Aug. 19, 2014

(54) PROTON DECOUPLED HYPERPOLARIZED MAGNETIC RESONANCE IMAGING

(75) Inventor: Ralph E. Hurd, Milpitas, CA (US)

(73) Assignee: General Electric Company, Schenectady, NY (US)

( * ) Notice: Subject to any disclaimer, the term of this patent is extended or adjusted under 35 U.S.C. 154(b) by 2174 days.

(21) Appl. No.: 11/562,394

(22) Filed: Nov. 21, 2006

(65) Prior Publication Data

US 2008/0116890 A1    May 22, 2008

(51) Int. Cl.
    *A61B 5/05*      (2006.01)

(52) U.S. Cl.
    USPC .............. 600/410; 600/420; 324/311

(58) Field of Classification Search
    USPC .......... 324/307, 311–313, 318–322; 600/410, 600/420
    See application file for complete search history.

(56) References Cited

U.S. PATENT DOCUMENTS

| 4,689,561 | A | * | 8/1987 | Seto et al. .............. | 324/307 |
| 2002/0011842 | A1 | | 1/2002 | Fiat | |
| 2008/0211499 | A1 | * | 9/2008 | Foxall et al. .......... | 324/311 |

FOREIGN PATENT DOCUMENTS

| JP | 2004-503786 A | 2/2004 |
| WO | WO 0196895 A1 | 12/2001 |
| WO | 2005036197 A1 | 4/2005 |
| WO | 2006011810 A2 | 2/2006 |

OTHER PUBLICATIONS

Mansson et al., "13C imaging—a new diagnostic platform," Eur Radiol (2006) 16: 57-67.
Golman et al., "Molecular Imaging With Endogenous Substances," PNAS, Oct. 2, 2003, vol. 100, No. 18, pp. 10435-10439.
Golman et al., "Real-Time Metabolic Imaging," PNAS, Jun. 25, 2006, vol. 103, No. 30, pp. 11270-11275.
Golman et al., "Metabolic Imaging and Other Applications of Hyperpolarized 13C," Acad Radiol (2006) 13: 932-942.
Golman et al., "Molecular Imaging Using Hyperpolarized 13C," The British Journal of Radiology (2003), 76: S118-S127.
Beckmann et al.; 13C NMR for the Assessment of Human Brain Glucose Metabolism in Vivo; Biochemistry, 30, pp. 6362-6366; 1991.
Coutts et al.; Proton Decoupling in Whole Body Carbon-13 MRS; Encyclopedia of Nuclear Magnetic Resonance, 6, pp. 3829-3832; 1996.
Mayer et al.; Fast Metabolic Imaging of Systems with Sparse Spectra: Application for Hyperpolarized 13C Imaging; Proceedings of the International Society for Magnetic Resonance in Medicine, 14th Meeting Proceedings, May 6, 2006.

* cited by examiner

*Primary Examiner* — Unsu Jung
*Assistant Examiner* — Daniel Huntley
(74) *Attorney, Agent, or Firm* — Ziolkowski Patent Solutions Group, SC

(57) ABSTRACT

A system and method for improving available signal-to-noise ratio (SNR) and speed of MR imaging of hyperpolarized substances is disclosed. The system and method include decoupling spin effects of hydrogen nuclei from non-hydrogen nuclei of interest during sampling of MR signals therefrom. Though the hydrogen nuclei of the hyperpolarized substance may not be directly bonded to the non-hydrogen nuclei of interest, resonance splitting may still impact SNR. Long range decoupling improves T2* time, and thus preserves signal strength and available SNR.

7 Claims, 5 Drawing Sheets

PROTON DECOUPLED HYPERPOLARIZED MAGNETIC RESONANCE IMAGING

BACKGROUND OF THE INVENTION

The present invention relates generally to a system and method for magnetic resonance (MR) imaging of hyperpolarized substances and, more particularly, to a method of decreasing undesirable effects of proton coupling on available signal-to-noise ratio (SNR) for hyperpolarized contrast agent imaging.

When substances such as human tissue or contrast agents are subjected to a uniform magnetic field (polarizing field $B_0$), the individual magnetic moments of the spins in the substances attempt to align with this polarizing field, but precess about it in random order at their characteristic Larmor frequency. If a substance, contrast agent, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The set of received nuclear magnetic resonance (NMR) signals resulting from a scan sequence is digitized and sent to a data processing unit for image reconstruction using one of many well known reconstruction techniques.

Imaging with MR contrast agents can be done in multiple ways. Certain substances, known as paramagnetic contrast agents, increase the magnetization and/or polarization of surrounding substances, and are therefore not themselves a source of MR signals. Other contrast agents contain excitable non-hydrogen nuclei, such as $^{13}C$, $^{14}N$, $^{31}P$, $^{19}F$, and $^{23}Na$, which produce their own MR signals, rather than increasing MR signal strength of surrounding tissues. Several methods of enriching and hyperpolarizing such substances have been developed to further increase signal strength and imagability thereof.

One drawback of conventional methods of imaging non-hydrogen nuclei is the effect that spin interactions can have on available SNR. For example, the coupling between spins of a hydrogen proton and a directly bonded carbon-13 isotope can cause resonance frequency splitting. Thus, the spectral profile of a substance having a bonded or "protonated" carbon will appear wider and weaker. This splitting generally results in a spectral profile having a number of "peaks" of varying and predictable strength, proportionate to the coupling constant of the interacting spins of the substance. Accordingly, resolution of an image can be affected when resonant frequencies to be imaged are nearby, since spectral profiles can overlap, cancel, or enhance one another.

One method of overcoming this drawback in substances having protonated carbons (or other imagable nuclei) is known as proton decoupling. These methods typically include the use of a saturating B1 excitation field to reduce or eliminate the effect of proton spins on the resonance of other excitable nuclei of interest. Most non-hyperpolarized $^{13}C$ applications utilize such an approach. Since the relevant spectra of these compounds can be relatively close, proton decoupling is used to provide an increase in image resolution. However, these methods are not known to be used in imaging of hyperpolarized substances or substances with non-protonated nuclei of interest. When imaging hyperpolarized substances, sharply declining free induction decay (FID) signal strengths and FID signals of lowered initial strength can limit available sampling time and SNR. Additionally, because of the susceptibility of hyperpolarization to destruction from RF pulses, increasing flip angles may not adequately compensate for reduced sampling time or SNR.

It would therefore be desirable to have a system and method which overcomes the aforementioned drawbacks of non-hydrogen and hyperpolarized imaging. In particular, it would be desirable for such a system and method to improve T2* decay rate and signal strength of hyperpolarized substances for increased available sampling time and SNR.

BRIEF DESCRIPTION OF THE INVENTION

A system and method for increasing available SNR in hyperpolarized metabolic imaging are provided. By decoupling the effects of proton spins on imagable non-hydrogen nuclei during sampling thereof, signal strength decays less rapidly and available SNR is increased.

In accordance with one aspect of the present invention, an MR system includes a plurality of gradient coils positioned about a bore of a magnet to impress a polarizing field, an RF coil assembly coupled to a pulse generator to emit an RF pulse sequence and arranged to receive resulting MR signals from a subject within the bore, and a system control coupled to the plurality of gradient coils and the RF coil assembly, the system control configured to control operation of the plurality of gradient coils and the RF coil assembly and programmed to cause a long-range decoupling during sampling of MR signals from non-hydrogen nuclei.

In accordance with another aspect of the invention, a method for MR imaging is disclosed. The method includes introducing an MR contrast agent to a subject of interest, acquiring MR signals from at least the contrast agent, and, during the acquisition of MR signals, saturating hydrogen nuclei to improve an SNR of the acquisition.

According to a further aspect of the invention, a set of instructions is stored on a data storage medium. The instructions, when executed by a computer, cause the computer to excite nuclei of a hyperpolarized substance, decrease a resonance splitting of the hyperpolarized substance, and sample MR signals from the nuclei for image reconstruction.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION OF THE PREFERRED EMBODIMENT

The following description includes a discussion with reference to a preferred embodiment involving the excitation and imaging of substances containing $^{13}C$ nuclei. However, it is to be understood that the system and method described herein find corresponding and equivalent applicability in the imaging of other non-hydrogen nuclei, such as $^{15}N$, $^{31}P$, $^{19}F$, and $^{23}Na$ nuclei as well as other well-known excitable nuclei having a net spin. In addition, the system and method need not be limited to imaging of metabolic processes. Imaging of individual or non-interacting substances which experience the effects of long range proton coupling may also benefit from the features described herein. Furthermore, the system and method as applied to non-hydrogen excitable nuclei does not preclude its use in combination with, or augmented by, traditional hydrogen imaging.

Figure 1:
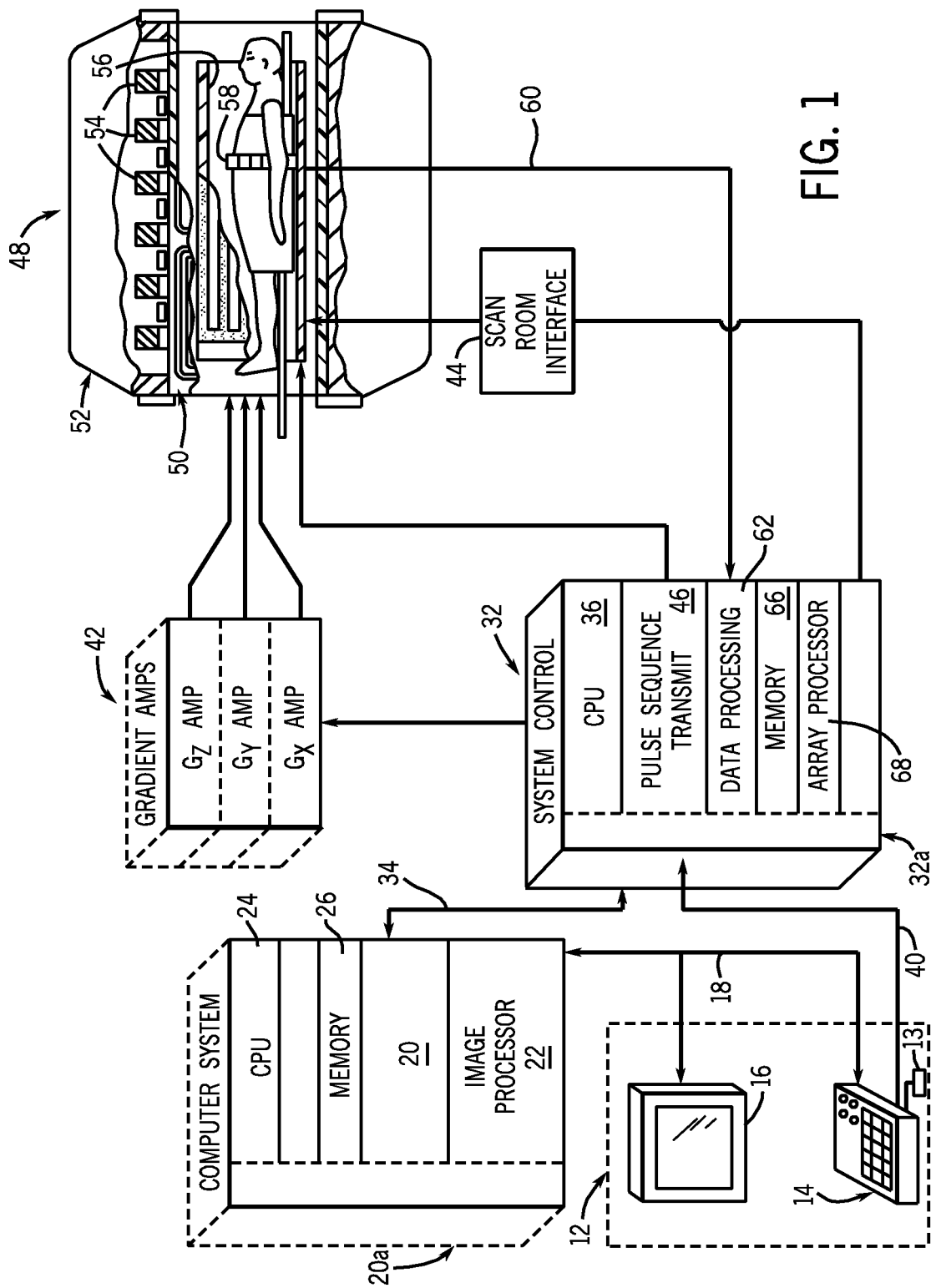
FIG. 1 is a schematic block diagram of an exemplary MR imaging system in accordance with an embodiment of the present invention.

Referring now to FIG. 1, the major components of an example magnetic resonance imaging (MRI) system 10 incorporating an embodiment of the present invention are shown. The operation of the system may be controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, which may include a frame buffer for storing image data arrays. The computer system 20 may also be connected to permanent or back-up memory storage, a network, or may communicate with a separate system control 32 through a high speed serial link 34. The input device 13 can include a mouse, keyboard, track ball, touch activated screen, light wand, or any similar or equivalent input device, and may be used for interactive geometry prescription.

The system control 32 includes a set of modules connected together by a backplane 32a and connected to the operator console 12 through a serial link 40. It is through link 40 that the system control 32 receives commands from the operator to indicate the scan sequence that is to be performed. The pulse sequence transmit module 38 commands the scanner components to carry out the desired scan sequence, by sending instructions, commands, and/or requests describing the timing, strength and shape of the RF pulses and pulse sequences to be produced, to correspond to the timing and length of the data acquisition window. The system control 32 also connects to a set of gradient amplifiers 42, to indicate the timing and shape of the gradient pulses that are produced during the scan. The system control 32 may also receive patient data from a scan room interface 44, which may relate data from a user or from a number of different sensors connected to the patient, such as ECG signals from electrodes attached to the patient.

The gradient waveform instructions produced by system control 32 are sent to the gradient amplifier system 42 having Gx, Gy, and Gz amplifiers. Amplifiers 42 may be external of scanner 48, or may be integrated therein. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and an RF coil assembly 56, 58. RF coil assembly may include a whole-body RF transmit coil 56, surface or parallel imaging coils 58, or both. The coils 56, 58 of the RF coil assembly may be configured for both transmitting and receiving, or for transmit-only or receive-only. A pulse generator (not shown) integrated into the scanner equipment 48 produces RF pulses in accordance with the instructions of the pulse sequence transmit module 46 which are amplified and coupled to the RF coil 56 for transmission. Alternatively, RF transmit coil 56 may be replaced or augmented with surface and/or parallel transmit coils, such as coil 58. Similarly, the resulting signals emitted by the excited nuclei in the patient may be sensed by separate receive coils, such as parallel coils or surface coils 58, and are then sent over a data link 60. The MR signals are demodulated, filtered, and digitized in the data processing section 62 of the system control 32.

A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory 26. In response to commands received from the operator console 12, this image data may be archived in long term storage or may be further processed by the image processor 22 and conveyed to the operator console 12 and presented on the display 16.

Figure 2:
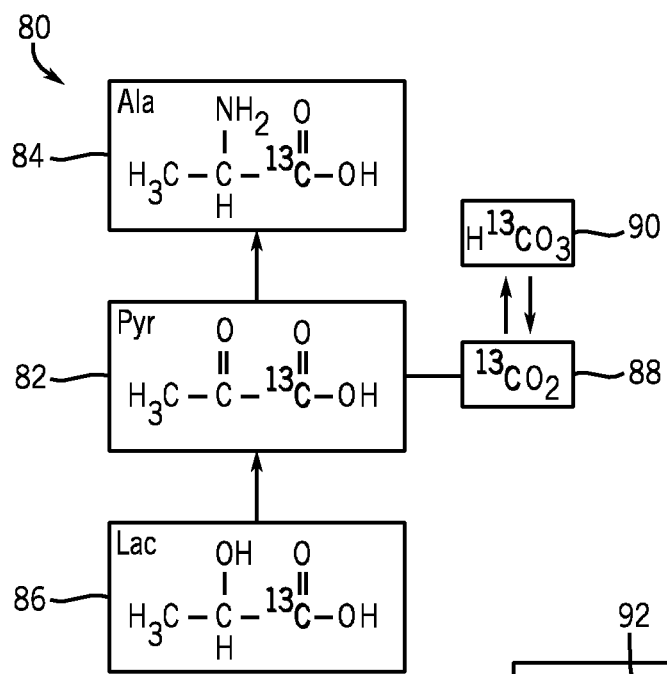
FIG. 2 is a diagram of a metabolic process involving a $^{13}C$ labeled pyruvate.

Referring now to FIG. 2, a metabolic process 80 of $^{13}C$ labeled pyruvate is depicted. As mentioned above, this metabolic process 80 and the particular nuclei involved therein are merely a preferred embodiment, and many alternative excitable nuclei, substances, and/or processes may be equivalently imaged according to various embodiments of the present invention. Pyruvate is an intermediate common to two major metabolic/catabolic pathways in mammalian cells—transamination to alanine and reduction to lactate. Metabolic imaging of $^{13}C$ labeled pyruvate is an important tool for monitoring metabolite levels as well as organ function and disease quantification.

As shown, the $^{13}C$ isotope of the pyruvate molecule 82 is not directly bonded to a hydrogen atom. The $^{13}C$ isotope is only indirectly coupled to hydrogen atoms (protons) of the $C_3$ methyl. The resulting coupling is weak, since the coupled hydrogen is three bond lengths away from the $^{13}C$ atom. The 3JCH coupling for such a $^{13}C$ pyruvate molecule 82 is approximately 1 Hz. The pyruvate molecule 82 is intentionally $^{13}C$ enriched at this carbon position to take advantage of the longer resulting T1 polarization lifetime.

When $^{13}C$ pyruvate molecule 82 is introduced into a subject of interest, nearly all of the compound will be metabolized. A small portion will become pyruvate hydrate (not shown) in solution, which is not metabolically active. The remaining portion of the $^{13}C$ pyruvate will be metabolized into either $^{13}C$ alanine 84 or $^{13}C$ lactate 86. A byproduct of this reaction is carbon dioxide 88 which may have an equilibrium exchange with bicarbonate 90.

In contrast to pyruvate, the alanine 84 and lactate 86 molecules have $^{13}C$ isotopes which are much more strongly coupled with nearby hydrogen atoms, though the $^{13}C$ atoms are still not directly bonded to hydrogen atoms. The 2JCH and 3JCH coupling constants therein are approximately 4 Hz.

Figure 3:
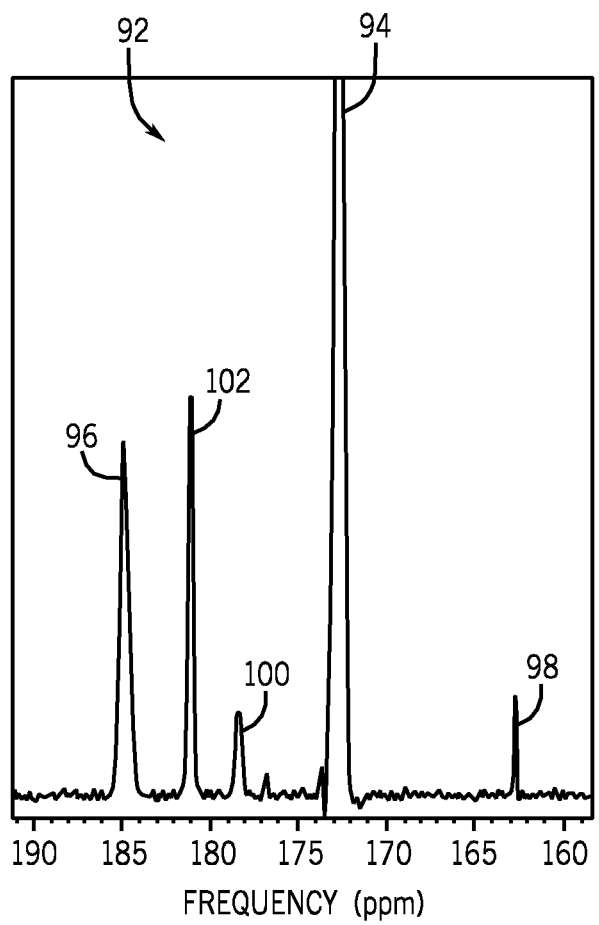
FIG. 3 is a graph of spectral excitation profiles for the metabolic process of FIG. 2.

FIG. 3 shows a spectral profile graph 92 of MR signal strength illustrating the effects of proton coupling. The highest spectral peak 94 represents the signal strength of administered hyperpolarized $^{13}$C pyruvate. Since coupling between the $^{13}$C labeled carbon nucleus and relevant hydrogen nuclei is weak in pyruvate, signal strength is preserved because little or no resonance splitting occurs. Peak 102 represents signal strength from pyruvate hydrate, which is still higher than the peaks of lactate 96 and alanine 100, despite the relative sparsity of pyruvate hydrate molecules. In comparison to their respective heights, the linewidths of lactate 96 and alanine 100 are increased proportionately to that of pyruvate 94 and pyruvate hydrate 102. That is, the pyruvate 94 and pyruvate hydrate 102 peaks are proportionately slimmer than those of alanine 100 and lactate 96. Thus, the effects of resonance splitting from the increased 2JCH and 3JCH coupling are apparent.

Figure 4:
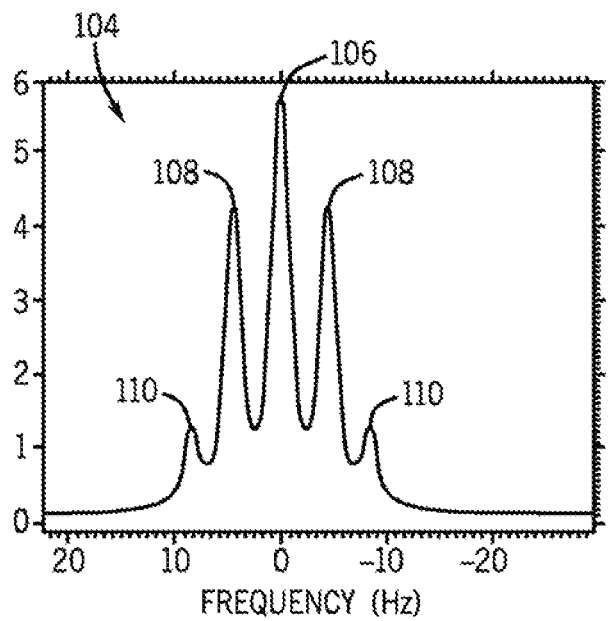
FIG. 4 is a graph of a spectral excitation profile showing the resonance splitting effects of proton coupling.

FIG. 4 is a more detailed view of a spectral frequency profile 104 showing the effects of resonance splitting from proton coupling. Primary peak 106 occurs at 0 Hz from the excited resonance frequency of interest, secondary peaks 108 occur at approximately 5 Hz from the resonance frequency, and tertiary peaks 110 occur at approximately 9 Hz from the resonance frequency. Despite the relative spreading of this profile 104 from the expected resonance frequency, the spectra of substances of interest in typical hyperpolarized imaging techniques are sparse enough that resolution is not substantially affected. However, as will be shown below, long range proton coupling, while not a substantial limit on resolution, does affect T2* time and thus available SNR for sampling.

Figure 5:
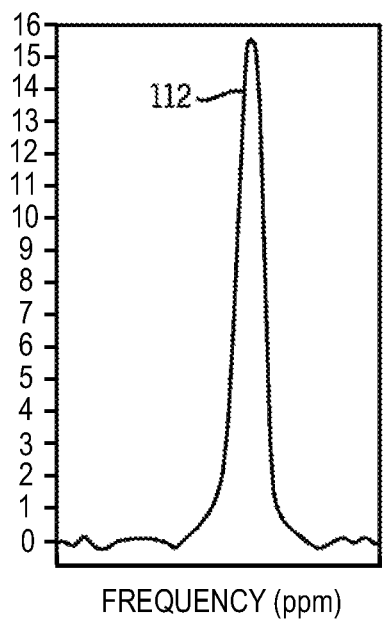
FIG. 5 is a graph of a spectral excitation profile showing the effects of proton decoupling in accordance with an embodiment of the present invention.

Referring now to FIG. 5, the result of decoupling in accordance with an embodiment of the present invention is shown. The decoupled spectral frequency profile 112 of FIG. 5 is generated by the same substance, yet does not exhibit the frequency splitting/spreading effects displayed in FIG. 4. Rather, the profile 112 of FIG. 5 has a much narrower linewidth, especially in light of the improved peak signal strength. Multiple methods of proton decoupling similar to those used in $^{13}$C imaging may be used to achieve such an improved spectral frequency profile 112 in hyperpolarized imaging. In most methods, the decoupling is achieved by applying a B1 field keyed to the resonance of protons. This field is normally used to decouple or saturate hydrogen nuclei directly bonded to imaged nuclei to reduce or eliminate the effects of spin-spin coupling on resulting signals of the imaged nuclei. In an embodiment of the present invention, a B1 proton excitation or saturation field may be used to decouple spin-spin effects of hydrogen nuclei on non-hydrogen excitable nuclei (such as $^{13}$C) that are more than one bond length apart. For example, the decoupling may be applied to decouple the 2JCH and 3JCH effects of hydrogen nuclei on $^{13}$C nuclei in hyperpolarized alanine and lactate metabolites.

Figure 6:
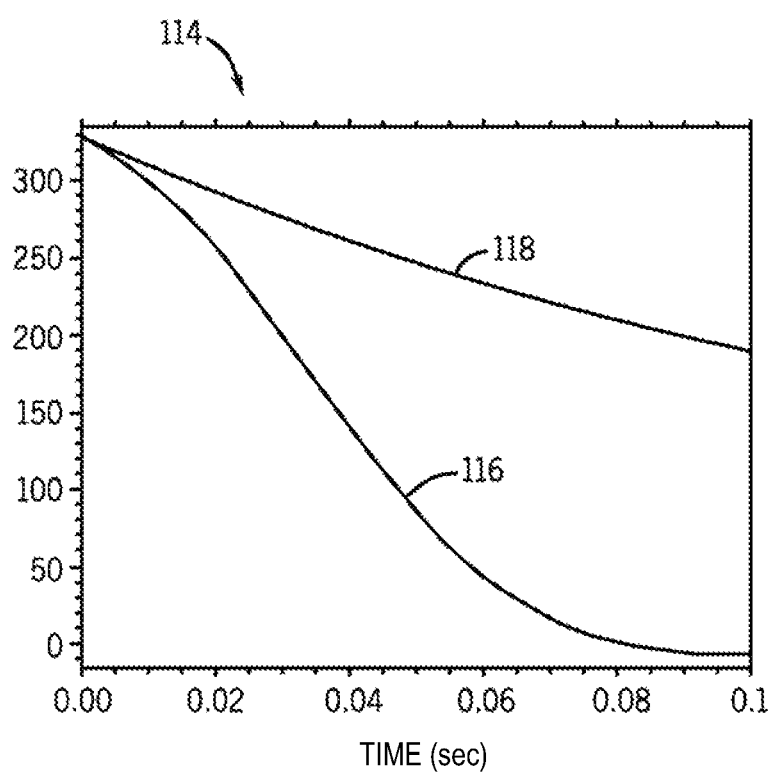
FIG. 6 is a graph of MR signal strength over time for coupled and decoupled imaging.

FIG. 6 is a graph of MR signal strength over time for coupled and decoupled imaging. As mentioned above, long range decoupling for hyperpolarized substances at non-protonated nuclei decreases or eliminates resonance splitting and improves signal strength at the expected resonance frequency. Long range decoupling also significantly (and unexpectedly) improves T2* relaxation times for hyperpolarized substances. The graph 114 of FID signal over time illustrates how JCH effects dominate available SNR. As known in the art, for each data acquisition of MR signals from a substance to be mathematically useful to an average or sampling, the signal strength must be greater than the square root of the noise signal. Therefore, when the FID signal decays past a certain point, data can no longer be usefully sampled. In other words, useful SNR or FID signal of sufficient strength, exists for a period of time proportionate to the T2* decay rate.

As shown in FIG. 6, the decay rate 116 for proton coupled hyperpolarized substances is much faster and declines much more sharply than the decay rate 118 for decoupled hyperpolarized substances. Thus, the point at which the FID signal equals the square root of the noise signal (at which time there is no available SNR) is reached much more quickly when decoupling is not applied 116. In practice, available and useful SNR often exists for coupled, hyperpolarized $^{13}$C pyruvate and metabolites for only about 28 ms. Therefore, it becomes difficult to use higher resolution samplings which take longer acquisition periods. Contrastingly, the decay rate 118 for decoupled hyperpolarized substances remains higher for a longer period of time. Thus, longer, higher-resolution sampling sequences are possible. Similarly, since higher signal strength is achieved for a longer period of time through decoupling, higher flip angle RF pulses in faster sequences may be employed with the decoupling, to more efficiently utilize the magnetization of a hyperpolarized substance.

Figure 7:
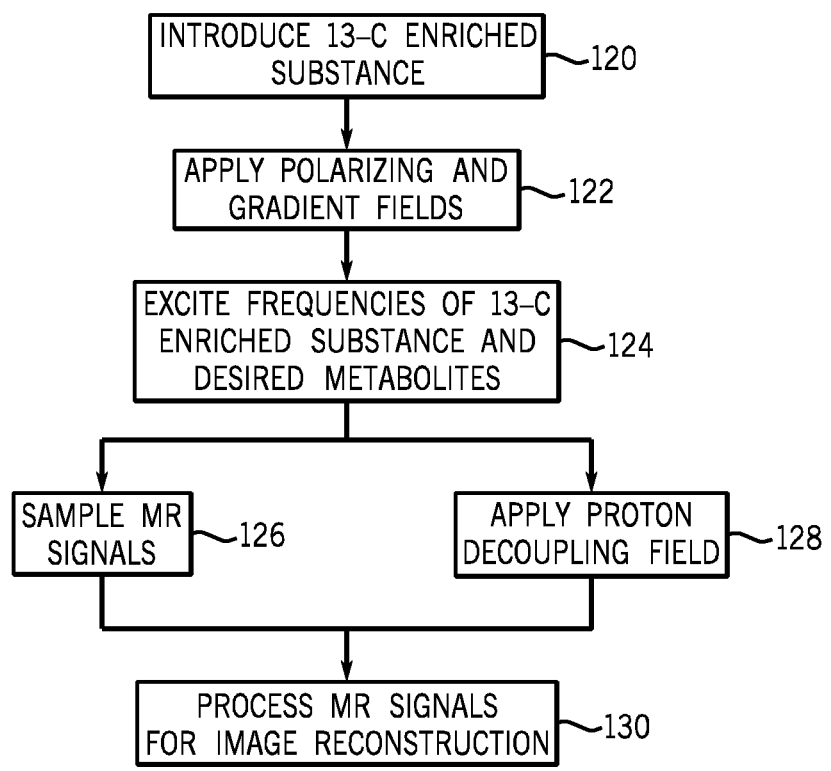
FIG. 7 is a flowchart illustrating a process for imaging hyperpolarized agents with proton decoupling in accordance with an embodiment of the present invention.

FIG. 7 is a flowchart illustrating a process for hyperpolarized imaging with proton decoupling in accordance with an embodiment of the present invention. The technique begins with administration of a hyperpolarized contrast agent into a subject of interest at block 120. Polarizing and gradient fields are then applied to prepare spins for encoding at block 122. The resonant frequencies of the hyperpolarized contrast agent and metabolites of interest thereof are then excited at block 124. In a preferred embodiment, these frequencies correspond to the resonant frequencies of hyperpolarized substances such as pyruvate, which are $^{13}$C enriched at non-protonated carbon positions, and metabolites like alanine, lactate, and bicarbonate. During the signal sampling portion of the acquisition sequence at block 126, a proton decoupling B1 field is applied to reduce or eliminate the resonance splitting effects of spin-spin coupling on the non-protonated $^{13}$C nuclei at block 128. After the desired amount of MR data is acquired (during an improved T2* time), the data is processed for image reconstruction at block 130. One or more of several well-known methods for image reconstruction may be used.

Accordingly, in one embodiment of the present invention, an MR system is provided that includes a plurality of gradient coils positioned about a bore of a magnet to impress a polarizing field, an RF coil assembly, and a system control. The RF coil assembly is coupled to a pulse generator to emit an RF pulse sequence and is arranged to receive resulting MR signals from a subject within the bore. The system control is coupled to the plurality of RF coils and the RF coil assembly to control operation of the plurality of gradient coils and the RF coil assembly and is programmed to cause a long-range decoupling during sampling of MR signals from non-hydrogen nuclei.

In another embodiment of the present invention, a method for MR imaging includes introducing an MR contrast agent into a subject of interest, acquiring MR signals from at least the contrast agent, and, during the acquisition of MR signals, saturating hydrogen nuclei to improve a signal-to-noise ratio of the acquisition.

In a further embodiment of the present invention, a data storage medium has a set of instructions stored thereon which, when executed by a computer, causes it to excite nuclei of a hyperpolarized substance, decrease a resonance splitting of the hyperpolarized substance, and sample MR signals from the nuclei for image reconstruction.

The present invention has been described in terms of the preferred embodiment, and it is recognized that equivalents, alternatives, and modifications, aside from those expressly stated, are possible and within the scope of the appending claims. The order and sequence of process or method steps may be varied or re-sequenced according to alternative embodiments.

What is claimed is:

1. A magnetic resonance (MR) imaging system comprising:
 a plurality of gradient coils positioned about a bore of a magnet to impress a polarizing field;
 an RF coil assembly coupled to a pulse generator to emit an RF pulse sequence and arranged to receive resulting MR signals from a subject within the bore; and
 a system control coupled to the plurality of gradient coils and to the RF coil assembly, the system control configured to control operation of the plurality of gradient coils and the RF coil assembly and programmed to sample MR signals during a sampling period and cause a long-range decoupling of protons from non-hydrogen nuclei during the sampling period, wherein the long-range decoupling comprises a long-range decoupling of protons that do not substantially affect resolution during the sampling period.

2. The MR imaging system of claim 1 wherein the system control that is programmed to cause the long-range decoupling is programmed to decouple protons from at least one of 13-C, 15-N, 31-P, and 19-F.

3. The MR imaging system of claim 1 wherein the system control that is programmed to cause the long-range decoupling is programmed to decouple protons which are not directly bonded to the non-hydrogen nuclei.

4. The MR imaging system of claim 3 wherein the system control is further programmed to cause the proton decoupling by causing a B1 excitation field to be generated and keyed to a resonance of hydrogen nuclei.

5. The MR imaging system of claim 1 wherein the non-hydrogen nuclei are enriched within a metabolic contrast agent.

6. The MR imaging system of claim 5 wherein the system control is further programmed to sample MR data for the metabolic contrast agent and at least one metabolite of the metabolic contrast agent.

7. The MR imaging system of claim 1 wherein the system control that is programmed to cause the long-range decoupling increases a $T2^*$ time of a substance containing the non-hydrogen nuclei by diminishing an effect of carbon-hydrogen coupling on a spectral profile of the substance.

* * * * *